(12) United States Patent
Brown et al.

(10) Patent No.: US 12,303,476 B2
(45) Date of Patent: May 20, 2025

(54) COMPOSITIONS AND METHODS OF ACHIEVING PAIN RELIEF

(71) Applicant: NeoHack Life Sciences LLC, Dallas, TX (US)

(72) Inventors: Dale G. Brown, Wharton, TX (US); Ira D. Hill, Austin, TX (US)

(73) Assignee: NeoHack Life Sciences LLC, Austin, TX (US)

( * ) Notice: Subject to any disclaimer, the term of this patent is extended or adjusted under 35 U.S.C. 154(b) by 0 days.

(21) Appl. No.: 18/383,606

(22) Filed: Oct. 25, 2023

(65) Prior Publication Data

US 2024/0165057 A1 May 23, 2024

Related U.S. Application Data

(60) Division of application No. 17/676,339, filed on Feb. 21, 2022, now abandoned, which is a continuation-in-part of application No. 16/408,504, filed on May 10, 2019, now abandoned, which is a continuation of application No. PCT/US2018/034296, filed on May 24, 2018.

(60) Provisional application No. 62/522,336, filed on Jun. 20, 2017.

(51) Int. Cl.
| | |
|---|---|
| A61K 36/00 | (2006.01) |
| A61K 31/015 | (2006.01) |
| A61K 31/045 | (2006.01) |
| A61K 31/16 | (2006.01) |
| A61K 31/164 | (2006.01) |
| A61P 23/02 | (2006.01) |

(52) U.S. Cl.
CPC ............ *A61K 31/16* (2013.01); *A61K 31/015* (2013.01); *A61K 31/045* (2013.01); *A61K 31/164* (2013.01); *A61P 23/02* (2018.01)

(58) Field of Classification Search
None
See application file for complete search history.

(56) References Cited

PUBLICATIONS

Celebi et al. (2013) Annals of Otology, Rhinology & Laryngology 122(7): 464-467. (Year: 2013).*
Kuwahuta et al. (2012) Pharmacology & Pharmacy , 3, 397-403. (Year: 2012).*
Nomura et al. (2012) J. Ethnopharmacology, 150: 583-589. (Year: 2012).*
Olah et al. (2017) Phytomedicine 34: 44-49. (Year: 2017).*
Patel et al. (2007) J. Am. Dermatol. 57: 873-8. (Year: 2007).*
Park, Chu-Kyu, et el., Receptor Potential Subtype V1/A1, Inflammatory Pain, and Spinal Cord Synaptic Plasticity in Mice: Distinct Roles of Resolvin D1, D2, and E1; The Journal of Neuroscience, Dec. 14, 2011 • 31(50):18433- 18438.
Paulraj, Jayaraj, et al., The Genus Spilanthes Ethnopharmacology, Phytochemistry, and Pharmacological Properties: A Review; Advances in Pharmacological Sciences vol. 2013, Article ID 510298, 22 pp.
Paulsen, Candice E., et al., Structure of the TRPA1 ion channel suggests regulatory mechanisms; Nature 520, 511-517 (2015); doi:10.1038/nature14367.
Bourinet, Emmanuel, et al., Calcimu-Permeable Ion Channels in Pain Signaling; Physiol Rev 94: 81-140, 2014 doi:10.1152/physrev. 00023.2013.
Mickle Aaron D. et al., Nociceptive TRP Channels: Sensory Detectors and Transducers in Multiple Pain Pathologies, Pharmaceuticals, Nov. 14, 2016;9(4): 72, doi: 10.3390/ph9040072.
Weng et al., Tmem100 is a regulator of TRPA1-TRPV1 complex and contributes to persistent pain, Neuron, Feb. 18, 2015;85(4): 833-846. doi:10.1016/j.neuron.2014.12.065.
Boonen et a, Transdermal behaviour of the N-alkylamide spilanthol (affinin) from Spilanthes acmella (Compositae) extracts, J. Ethnopharmacology, vol. 127, Issue 1, Jan. 8, 2010, 77-84.
De Spiegeleer et al., Skin penetration enhancing properties of the plant N-alkylamide spilanthol, J Ethnopharmacol. Volume 148 Issue 1, Jun. 21, 2013, 117-25, doi: 10.1016/j.jep.2013.03.076.
Wu et al., Anti-inflammatory Effect of Spilanthol from Spilanthes acmella on Murine Macrophage by Down-Regulating LPS-Induced Inflammatory Mediators, J. Ag. Food Chem., 2008, 56, 7, 2341-2349 Mar. 6, 2008.
Oeckinghaus and Ghosh, The NF-kappaB family of transcription factors and its regulation, Cold Spring Harb. Prospect. Biol., 2009, 1, a000034.

* cited by examiner

*Primary Examiner* — Russell G Fiebig
(74) *Attorney, Agent, or Firm* — Ladner Patent Management LLC

(57) ABSTRACT

In one aspect, this invention relates to a method for treating pain and subsequent resulting conditions. In yet another aspect, this invention relates to formulating agents to rapidly reverse painful conditions.

20 Claims, No Drawings

COMPOSITIONS AND METHODS OF ACHIEVING PAIN RELIEF

CROSS-REFERENCE TO RELATED APPLICATIONS

This application is a divisional of commonly owned copending U.S. patent application Ser. No. 17/676,339 filed Feb. 21, 2022. The '339 Application is a continuation-in-part of commonly owned copending U.S. patent application Ser. No. 16/408,504 filed May 10, 2019. The '504 Application is a continuation of PCT Application No. PCT/US18/34296, filed 24 May 2018. The PCT Application claims domestic priority under 35 U.S.C. 119(e) to U.S. Provisional Application Ser. No. 62/522,336, filed Jun. 20, 2017. The disclosures of these applications are hereby incorporated herein by reference.

FIELD OF THE INVENTION

In one aspect, this invention relates to method useful for treating pain and subsequent resulting conditions. In yet another aspect, this invention relates to formulating an agent to return humans to a less painful condition.

BACKGROUND OF THE INVENTION

The physical body of mammals utilizes control pathways for cell division, differentiation, wound repair, senescence; bacterial, viral, and fungal infections; cancer and brain memory functionality, and essentially all mammalian metabolism and bodily functions.

Pain control circuits have set points, regulated variables, control variables and controller gain (amplified response rate). Perturbation of mammalian systems results in a bodily response to return the system to a point of no pain. These perturbations may take the form of uncontrolled growth (cancer), uncontrolled energy substrates (diabetes), loss of memory control (Alzheimer's), wounds, itching, viral infections, bacterial infections, fungal infections, immune dis-regulation (lupus, Sjogren's Syndrome, Crohn's disease, irritable bowel disease), blood pressure deviation, acute inflammation, chronic inflammation, burns (x-rays, sunburn, thermal burns), aging cells, loss of hair follicle production, joint inflammation (rheumatoid arthritis, osteoarthritis), psoriasis, eczema, atopic dermatitis, mucositis, painful scarring, Aphthous ulcers, rosacea, and the like.

Loss of control to a mammalian system can have catastrophic results, i.e., death. In most instances, loss of homeostatic control results in an attempt to return the mammalian system to the particular set point, i.e., pain free condition. Areas of immediate control are oxygenation levels in the blood; nerve conduction in control of muscles, e.g., breathing; brain processing of feedback signals from touch, sight, and sound.

These acute systems require a quantitative sensor; a feedback mechanism for responding to the signal. Ion channels that control sodium, potassium and calcium ions entry to the cellular cytoplasm are of major importance to carrying out the function of the particular organ under study. Modulation of the acute system to external inputs allows a many-fold response to touch, pain, heat, pH and diseases states.

Restoring a pain-free system to the set point is accomplished by healing mechanisms through responding to acute and chronic set points.

SUMMARY OF THE INVENTION

In one aspect of the invention, there are provided methods for returning a human to a healthy pain-free state, by administration of an effective amount of the pain-relief compositions of the present invention to a patient in need of such treatment.

Mammalian dis-regulations, such as: oral pain, joint pain, diabetic wounds, high blood pressure, and stem cell functionality, cold sores, thrush, shingles, coronavirus infections, Alzheimer's disease, cancer, radiation dermatitis, burns, Crohn's disease, psoriasis, scar formation, inflammation, pruritus, Sjogren's Syndrome, insect bites and stings (with or without accompanying anaphylactic shock) and various other allergic responses to foods, pollens, environmental allergens, etc., are treated with compositions to help return the mammal to the respective pain-free condition.

Definitions

As used herein, PAIN-FREE is defined as: "The tendency of a system, especially the physiological system of higher animals, to maintain internal stability, owing to the coordinated response of it parts to any situation or stimulus that would tend to disturb its normal conditions or function." (The American Heritage® Science Dictionary, 5 th edition 2020).

EMBODIMENTS OF THE INVENTION

As described herein, one embodiment of the invention is a method comprising two or more additive components selected from the group consisting of herbal actives and nature-identical synthetic chemical entities. This composition may include a pharmaceutically acceptable carrier.

In an embodiment of the invention, a pharmaceutically acceptable carrier is formulated with a surfactant, which significantly improves bodily functions better than other surfactants. Preferred surfactants that can be formulated into a pharmaceutically acceptable carrier having these characteristics are: poloxamer 407, poloxamer 338, PEG/PPG-116/66 copolymer, PEG/PPG-38/8 Copolymer, 1-octadecanaminium, N,N-dimethyl-N-octadecyl-, chloride; either alone or together.

As described herein, one embodiment of the invention is a method of treating a subject in pain by administering an amount of a pain-relief composition comprising the isobutylamides—spilanthol, pellitorine, and alpha-hydroxysanshool, optionally along with beta-caryophyllene and pro-vitamin B5.

In a method of the present invention, the painful condition may be caused by the entire spectrum of malfunctions, related to a body condition selected from the group consisting of, but not limited to: diabetes, arteriosclerosis, radiation dermatitis, pruritus, insect bites, allergic responses to allergens in pollens, foods, personal care products and chemical ingredients, insect stings (up to and including anaphylactic shock), carbuncles, dermal burns due to exposure to sun, x-rays and/or excessive heat, cancer, Sjogren's Syndrome, mucositis, aphthous ulcers, periodontal and gingivitis disease, Herpes simplex, Herpes zoster, coronavirus-19, yeast and/or microbial infections, psoriasis, Crohn's disease, lupus, irritable bowel disease, painful scarring, fibromyalgia, bruises, rheumatoid and osteoarthritis, and the like.

In a method of the present invention, the composition may be administered to the subject by a route selected from the group consisting of mucosal, dermal, oral, inhalation, injection, and other common routes known in the medical arts. In the method, the composition may include two or more alkylamides and other molecules therein which are effective for achieving a pain-free condition. In the method, the alkylamides may be selected from the group consisting of spilanthol, pellitorine, alpha-hydroxysanshool, and mixtures thereof.

In a method of the present invention, the composition may be administered to the subject prior to, immediately after, and/or long-after the painful condition develops.

In a method of the present invention, the inflammatory conditions are controlled by affecting one or more biochemical control systems selected from the group consisting of NRF2, NFkB, PI3K, AKT, p38-MAPK, JNK, PIP2, PIP3, ERK½, cAMP, Adenylyl cyclase, Annexin A1, TRPV1, TRPA1, TRPM8, PGE2, TNFa, IL-1b, CXCR4, CXCL12 and CB2.

Although not wishing to be bound by the above mode of action, it is consistent with the human and in-vitro case history results presented herein as UTILITY EXAMPLES, which are adequate to encourage the use of the described mixtures utility for the desired relief of pain.

In a method of the present invention, the components may be administered in an amount from 0.01 mg to 1000 mg per dose.

In a method of the present invention, the vitamin is a pro-vitamin. In a preferred method, the vitamin may be pro-vitamin B5. In a preferred method, the vitamin may be administered at from 1.5 mg to 1000 mg per dose. In a more preferred method, the vitamin amount administered may be from 2.5 to 500 mg per dose.

The unexpected effect of the ingredients of menthol, spilanthol, pellitorine, beta-caryophyllene and pro-vitamin B5 is the rapid temporary relief of discomfort and pain.

It should be noted that the literature (both folk and scientific) is replete with examples of individual natural extracts containing active agents (and by extension—nature-identical molecules produced synthetically) benefitting various problematic pain and inflammatory symptoms. However, Applicant submits that the present invention, namely a combination of menthol, spilanthol, pellitorine, beta-caryophyllene including pro-vitamin B5 positively impacts a wide range of pain causing diseases and conditions, with both rapid and extensive relief, is both an unexpected and surprising discovery.

Preferred embodiments of the invention include the following:

1. A method for pain treatment by applying a composition comprising a mixture of spilanthol, pellitorine, and beta-caryophyllene.

2. The method of Embodiment 1, which may further contain menthol and/or pro-vitamin B5.

3. The method of Embodiment 1, wherein the painful condition is caused by or related to a body condition selected from the group consisting of: Chronic and Acute Pain of the muscles, joints and ligaments, Migraine Headaches, Diabetes, Arteriosclerosis, Radiation Dermatitis, Pruritus, Insect bites, Anaphylactic Shock from serious allergic responses to allergens, Food Allergies, Pollens and other Environmentally induced allergies, Carbuncles, painful scarring, Dermal burns due to exposure to sun, x-rays and/or excessive heat, Cancer, Mucositis, Aphthous ulcers, Periodontal and Gingivitis disease, Herpes simplex, Herpes zoster, coronavirus-19, Yeast and/or Microbial infections, Psoriasis, Crohn's disease, Lupus, Irritable Bowel disease, fibromyalgia, Rheumatoid and Osteoarthritis, and Xerostomia 4. The method of Embodiment 1, wherein said composition is administered to the subject by a route selected from the group consisting of mucosal, dermal, oral, inhalation, injection, and other common routes known in the medical arts.

5. The method of Embodiment 1, wherein the composition is administered to the subject prior to, immediately after, and/or long-after the homeostatic malfunction condition develops.

6. The method of Embodiment 1, wherein the painful conditions are controlled by affecting one or more biochemical control systems selected from the group consisting of Annexin A1, NRF2, NFkB, PI3K, AKT, p38-MAPK, JNK, PIP2, PIP3, ERK½, cAMP, Adenylyl cyclase, TRPV1, TRPA1, TRPM8, PGE2, IL-1b, CXCR4 and CXCL12 and CB2.

7. The method of Embodiment 1, wherein the alkylamides are administered in an amount from 0.1 mg to 1000 mg per dose and beta-caryophyllene is administered from 2 mg to 1000 mg per dose.

8. The method of Embodiment 2, wherein the pro-vitamin B5 is administered at from 2.5 mg to 1000 mg per dose and/or menthol is administered at 0.2 mg to 20 mg per dose.

It will be appreciated by those persons having ordinary skill in the art(s) to which the present invention relates that any of the features described herein in respect of any particular embodiment and/or embodiment of the present invention can be combined with one or more of any of the other features of any other embodiments and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

DETAILED DESCRIPTION OF THE PREFERRED EMBODIMENTS

Pain is a result of the loss of homeostatic regulation and constitutes an "unpleasant sensory and emotional experience associated with actual or potential tissue damage", (Mickle et al., Pharmaceuticals, 2016, vol. 9, article 72). Pain acts as an alarm system and a protective mechanism for a wide range of diseases and conditions due to a loss of homeostatic regulatory conditions, i.e., pathological conditions.

The first and foremost pain process is the peripheral detection and transduction of noxious stimuli that are determined as painful by the higher-order structures in the central nervous system. The terminology that has been widely used to define this process is "nociception", which accounts for the neural mechanisms and pathways for the encoding and processing of noxious stimuli.

Transient Receptor Channels (TRP) are ion channels used as sensory detectors and transducers of many pain pathologies, for example, inflammatory pain, dental pain, migraine, neuropathic pain, visceral pain, heat, acid, mechanical and temperature.

More specifically, calcium ion channels that control pain are TRPV1, TRPA1 and TRPM8. Antagonists and agonists act to sensitize or tamp down the response to pain. (Bourinet et al., Physiol. Rev. 2014, 94, 81-140).

Multiple control sites in the TRPA1 ion channel proteins allow modulation for high and low states of response to pain stimuli. (Paulsen et al., Nature, 2015, 520, 511-517).

Co-expression of TRPV1-A1 complexes in dorsal root ganglia (DRG) have been found to be regulated by the connector Tmem100 in the instance of complex and persistent pain. (Weng et al., Neuron, 2015, 85, 833-846).

The arachidonic pathway pain modulators have a major influence on the sensation of pain. Some endogenous inhibitors of pain have been shown to inhibit both TRPV1 and TRPA1 with potent pain relief activity. (Park et al., J. Neuroscience, 2011, 31 (50), From the above references, a suitable pain relief composition may be derived from those structures that affect pain by dermal and mucosal transport, or by oral ingestion. The dual ion channel approach would seem to be productive in relieving pain.

A pain relief composition may combine multiple control mechanisms to be effective. Suitable herbal actives with known ion channel and pain relief properties combined with other biochemical modifiers such as vitamins or their precursors has been found to exert pain relief rapidly and for extended periods of time.

Spilanthes species have reported pain relief properties in many review articles. Some species are called the "toothache plant". Paulraj et al., (Advances in Pharmacological Sciences, Volume 2013, article ID 510298), details worldwide use of the genus in traditional medicines for pain, cancer, cough, xerostomia, mouth ulcers, wound healing, infections, eczema, local anesthetic, and rheumatism.

It has been found that the alkylamides, spilanthol and pellitorine; beta-caryophyllene in combination with pro-vitamin B5 formulated in a suitable carrier give dermal and mucosal pain relief of a rapid nature. For example, oral sores such as canker sores, cold sore/fever blisters, and other infections by various viruses, bacteria and yeasts may be treated with sprays, rinses, lozenges, gels, and toothpastes containing these compounds to provide pain relief.

The ability of alkylamides to penetrate the skin and to enhance the penetration of other chemical structures has been demonstrated. (Boonen et al., J. Ethnopharma. 2010, 127, 77-84; De Spiegeleer et al, J. Ethnopharma. 2013, 148, 117-125). The primary pain-relieving agent in *Spilanthes* extracts is spilanthol, an isobutyl substituted unsaturated amide. The pain-relieving action is also accompanied by an anti-inflammatory activity operating through the NFkB inflammatory pathway. (Wu et al., J. Ag. Food Chem., 2008, The inflammatory pathways connected to NFkB regulate cancer, diabetes type 2, Alzheimer's, Sjogren's syndrome, wound healing, radiation dermatitis, rheumatoid arthritis, osteoarthritis, cold sores, shingles, pain, and aging. (Oeckinghaus and Ghosh, Cold Spring Harb Prespect Biol 2009, 1, a000034)

Testing of *spilanthes* extract and spilanthol and/or other extract ingredients such as pellitorine, in oral usage and in addition to beta-caryophyllene in dermal vehicles has shown a return to a less painful condition. In acute pain, a rapid reduction in inflammation and pain often occurs within minutes or hours; in chronic inflammation, positive results have been demonstrated after 2-3 weeks of oral or dermal applications.

Formulations for oral use range from 0.0025 wt % to 0.4 wt % spilanthol with 0.0015 wt % to 0.2 wt % pellitorine; and may further contain pro-vitamin B5 at from 0.1 wt % to 0.5 wt %, and menthol at 0.0005 wt % to 0.005 wt %.

Formulations for skin treatment include spilanthol at 0.1 wt % to 0.5% wt %, pellitorine at 0.05 wt % to 0.2 wt % and beta-caryophyllene at 1 wt % to 3 wt % in a vehicle compatible with pro-vitamin B5 at 2 wt % to 6 wt % with menthol at 0.02 wt % to 3 wt %.

Formulations for joint pain should include spilanthol and pellitorine at 0.05 wt % to 0.3 wt %, beta-caryophyllene at 1 wt % to 3 wt %, along with pro-vitamin B5 at 1.0 wt % to 6.0 wt % and menthol at 0.1 to 3 wt %.

FORMULATION EXAMPLES

Example 1—Skin Cream Lotion

A 500 mL stainless steel beaker fitted with an overhead stirrer was placed on a hot plate with 141.28 gm of water. The heat was adjusted to 85° C. with moderate stirring while 0.02 gm of sodium chloride was added. Colloidal oat kernel flour, 2.0 gm was added to the beaker with continued stirring for 5 minutes. Glycerin, 24 gm, was added followed by distearyldimonium chloride, 10 gm, white petrolatum, 8 gm, polydimethyl-siloxane, 350 centistokes (CS), 2.5 gm, cetyl alcohol, 5 gm and isopropyl palmitate, 6 gm, all with stirring for 10 minutes at the 85° C. temperature. The beaker was allowed to cool to 40° C. and benzyl alcohol, 1.2 gm was added with continued stirring. After cooling to 30° C., spilanthol, 0.95 gm, pellitorine, 0.75 gm, and menthol, 0.05 gm were added with slow stirring, followed by cooling to 25° C. The thick lotion was added to plastic tubes, which were suitable for dispensing onto skin.

Example 2—Oral Gel

A one Liter stainless steel beaker (tank A) was fitted with an overhead stirrer. Water, 266.265 gm, was added and moderate stirring began. Additional ingredients for this vessel were added: Sorbitol 70%, 204 gm; glycerin, 30 gm; potassium sorbate, 0.9 gm; sodium saccharin, 0.45 gm; sucralose, 1.2 gm; mint flavor, 2.0 gm; spilanthol, 0.12 gm and pellitorine, 0.08 gm; pro-vitamin B5, 1.0 gm were added with moderate stirring at room temperature.

A 250 mL beaker (tank B) containing an aqueous-free emulsion [PEG/PPG-116/66 polydimethylsiloxane (2.5 million CS)] (90:10) 19.08 gm, was heated to 95° C. with magnetic stirring.

To a 250 mL beaker (tank C), with overhead stirring and heating, was added propylene glycol, 60 gm, and methyl paraben, 0.9 gm. When the temperature attained 50° C., carboxymethylcellulose 9M31F, 15 gm, was added slowly over 3 minutes. After 5 minutes of stirring, the contents were added slowly to tank B, containing the emulsion. After continued stirring and cooling to 40° C., the contents of tank B were added to tank A slowly over 5 minutes. After an additional 30 minutes, the oral gel was packaged for dispensing from tubes to the oral cavity to stimulate saliva flow that relieved oral pain and give a pleasant mint tasting, tingling effect on the tongue.

Example 3—Pain Cream

A 500 mL stainless steel beaker fitted with an overhead stirrer was placed on a hot plate with 141.28 gm of water. The heat was adjusted to 85° C. with moderate stirring while 0.02 gm of sodium chloride was added. Colloidal oat kernel flour, 2.0 gm was added to the beaker with continued stirring for 5 minutes. Glycerin, 24 gm, was added followed by distearyldimonium chloride, 10 gm, white petrolatum, 8 gm, polydimethyl-siloxane, 50 CS, 2.5 gm, cetyl alcohol, 5 gm and isopropyl palmitate, 6 gm, all with stirring for 10 minutes at the 85° C. temperature. The beaker was allowed to cool to 40° C. and benzyl alcohol, 1.2 gm, was added with continued stirring. After cooling and stirring over 5 minutes to 30° C., pro-vitamin B5, 12 gm, spilanthol, 0.95 gm; menthol, 4.3 gm, pellitorine, 0.75 gm, and menthol, 0.05 gm were added with slow stirring until cooled to 25° C. The lotion was added to plastic tubes, jars or containers fitted with a treatment pump, which were suitable for dispensing onto skin. Application to sore and swollen joints gave an initial cooling with pain relief in minutes.

Example 4—Anti Inflammatory Cream

A 500 mL stainless steel beaker fitted with an overhead stirrer was placed on a hot plate with 141.28 gm of water. The heat was adjusted to 85° C. with moderate stirring while 0.02 gm of sodium chloride was added. Colloidal oat kernel flour, 2.0 gm was added to the beaker with continued stirring for 5 minutes. Glycerin, 24 gm, was added followed by distearyldimonium chloride, 10 gm, white petrolatum, 8 gm, polydimethyl-siloxane, 50 CS, 2.5 gm, cetyl alcohol, 5 gm and isopropyl palmitate, 6 gm, all with stirring for 10 minutes at the 85° C. temperature. The beaker was allowed to cool to 40° C. and benzyl alcohol, 1.2 gm, was added with continued stirring. After cooling and stirring over 5 minutes to 30° C., beta-caryophyllene; 6.45 gms, pro-vitamin B5, 12 gm; spilanthol, 0.95 gm; menthol, 4.3 gm and pellitorine, 0.75 gm were added with slow stirring until cooled to 25° C. The lotion was added to plastic tubes, jars or containers fitted with a treatment pump, which were suitable for dispensing onto skin. Application to sore and swollen joints gave an initial cooling with pain relief in minutes.

Example 5—Oral Compressed Tablet

A 4-quart Hobart mixer with oscillating spade blade was prepared for mixing the tablet formula. Isomalt (Beneo 720) 939.76 gm was added along with PEG/PPG-116/66, 30 gm, raspberry flavor, 3.0 gm, spilanthol, 0.35 gm, pellitorine, 0.125 gm, magnesium stearate, 15 gm, sucralose, 1.65 gm, pro-vitamin B5, 5 gm and citric acid powder, 5 gm. The mixer was stirred on low speed for 15 minutes. The resulting powder was added to a tablet press to give 1.5 gm tablets that delivered a raspberry flavor along with a tingling, pain relieving result.

Example 8—Lozenge

Hard cooked isomalt lozenges are prepared with a final dry weight formula comprised of: isomalt STM, 94.77 wt %; water, 2.08 wt %; poloxamer 407, 1.21 wt %; polydimethylsiloxane 2.5 million CS, 0.303 wt %; malic acid, 0.52 wt %; raspberry flavor, 0.31 wt %; sucralose 0.108 wt %; Acesulfame K, 0.052 wt %; spilanthol 0.005 wt %, pellitorine, 0.0015 wt %, menthol, 0.0001 wt % and FD&C Red No. 40, 0.0015 wt % of a 1 wt % solution. The lozenges have a tingling effect on the tongue and stimulate saliva flow, effectively moisturizing dry mouths and other uncomfortable or painful conditions.

Example 9—Oral Conditioning Rinse

A Rinse functioning as an Oral Conditioner and providing Dry Mouth Relief is prepared with (wt %): Water (86.31), PEG/PPG-116/66 (1.6), polydimethylsiloxane 2.5 mm CS (0.4), d-panthenol (0.5), Na Saccharin (0.03), Sucralose (0.05), Xylitol (5), Erythritol (3), Glycerin (2), Sodium Benzoate (0.5), EDTA (0.05), pellitorine (0.0015), menthol, (0.0001), spilanthol (0.004), Coolants WS 3 & 23 (0.005), citrus flavor (0.132), Sodium Carboxymethylcellulose (0.4). The resulting rinse soothes irritated oral mucosa, while stimulating saliva flow; effectively moisturizing dry mouths and other uncomfortable or painful conditions.

UTILITY EXAMPLES—BASED ON CASE HISTORIES

Example A

A 71 year old male had a brown scaly lesion on the scalp diagnosed as actinic keratosis. Prior episodes of these were removed surgically with resulting pain of surgical recovery. The lotion of Example 1 was supplied to the subject with directions to apply a pea-sized amount to the lesion twice daily. After three weeks, the lesion had disappeared and no painful conditions were present.

Example B

A 70 year old male had two brown scaly lesions on his forearm. The lotion of Example 1 was supplied to the subject with instructions to apply a small amount to the brown scaly lesions twice daily. After three weeks, the lesions had disappeared.

Example C

An 80 year old male was suffering from neoplasia of the sternum due to excessive X-ray and CAT scan treatment two years prior. Red irritated, itchy skin was present on his sternum. The subject applied small amounts of lotion from Example 1 to the red area twice daily for 3 weeks. The irritation and itching ceased within 24 hours of application. The skin returned to normal color after 3 weeks. No further lotion was applied, and the skin returned to normal color.

Example D

An 80 year old male with a history of wrestling injuries had extreme pain and swelling in his shoulders upon rising in the morning. A cream of Example 1 was given to the subject with instructions to use twice daily and pre-treat the shoulders with a menthol cream five minutes before using the cream of Example 1. Within 3 days, pain and swelling began to diminish. After 3 weeks of applications, swelling and pain were gone. No further cream was applied, and the symptoms did not return over the next several months.

Example E

A 60 year old female had both knees damaged by rheumatoid arthritis. She walked slowly with a cane or walker. Twice daily applications of a cream of Example 3 to both knees over 3 weeks gave substantial relief and allowed the subject to walk without cane or walker.

Example F

An 81 year old male had a history of cold sores (herpes). A tingling on the lip was a signal that an eruption was imminent. The subject applied the lotion of Example 1 to the tingling area on the lip at night. The next day no tingling was perceived. No eruption occurred and no redness or blisters appeared.

Example G

A 60 year old female incurred breast cancer procedure requiring 15 rounds of chemo and radiation following surgery. After ten days following the last radiation treatment, the surgical scar remained red, itchy and prevented normal sleep. Application twice daily of the lotion of Example 1 to the red area gave relief of itching within 4 hours. After three weeks of twice-daily application to the red irradiated area, it had returned to normal looking skin. No further lotion was applied.

Example H

A 70 year old male burned his finger with a soldering iron. The resulting blister was ⅜ inch long and ⅛ inch wide and tall. Pain was experienced from the burned area. Application of the lotion from Example 1 gave pain relief within 30 minutes. Twice daily application to the burned area for 7 days resulted in the skin of the blister flattening and re-attaching to the finger with no cracking or peeling of blister area.

Example I

A 70 year old male experienced fire ant bites on his legs. Typical itching and burning was experienced for 30 minutes after being bitten. Application of the lotion of Example 1 gave pain relief in one hour. Twice daily application to the bite area returned the skin to normal with no redness and no pustule formation as normally experienced with fire ant bites.

Example J

An 81 year old male experienced mosquito bites on his ankles and calves while on vacation. On returning to his hotel, he applied pea-sized amounts of the lotion of Example 1 to the bitten area about 1 hour after mosquito contacts. The itching was reduced very quickly, there was no further itching or redness as evidence. Subject reports that this experience was repeated throughout the mosquito season.

Example K

An 81 year old male experienced a serious sunburn on his nose, having forgotten to apply sunscreen to his nose while in the sun all day. In the evening, a red and painful sunburn was visually evident, hot, and painful to touch on the nose. Application of a small amount of the lotion from Example 1 to the affected area on the nose resulted in immediate (~30 sec) reduction in pain and temperature of the skin. The next morning the skin had lost its redness, was slightly tanned and was not sensitive to the touch. The skin never peeled off as expected.

Example L

A 73 year old male was scheduled to have Mohs surgery on his scalp to remove a basal cell carcinoma. One week prior to surgery, the subject applied twice daily a pea-sized amount of the lotion from Example 1 to the area scheduled for surgery. After surgery and one week recovery followed by removal of the stitches, the application of the lotion of Example 1 was resumed. After three weeks of twice-daily application of the lotion, the incision area was returned to normal skin with no evidence of painful scarring or surgical insult.

Example M

A 71 year old female was diagnosed with shingles on the lower jaw and on the scalp. A prescription for acyclovir was taken but no relief from pain or itching was forthcoming within 1 week. The subject was given the lotion of Example 1 with instructions to pre-treat the area with a menthol cream five minutes before applying the treatment cream. Twice daily application to the border of the shingles lesions along the axis of red streaks prevented further expansion of the shingle lesions. In areas of blisters that had not ruptured, application of the treatment cream caused the blisters to recede and not rupture. After three weeks of twice-daily treatment, the redness and pain were substantially gone. Episodes of recurring post-herpetic neuralgia were treated successfully over the next six weeks only with Example 1 cream giving reduction of redness, itching and pain.

Example N

A 72 year old female had a history of painful bruising of the skin resulting in black areas turning to blue, followed by green a then yellow before disappearing over 3 weeks. A black bruise area on the arm and leg were treated with the lotion of Example 1 twice daily over one week. The treatment resulted in the blue color rapidly fading to light green and no color or pain was observed after five days.

Example O

A 35 year male singer, had to frequently sip water between songs. Placement on of one tablet weighing 1.5 grams, formulated as per Example 5, between the cheek and lower gums prior to beginning the session and allowing it to dissolve while singing, then another after 20 minutes allowed a full program to be completed without repeated sips of water on stage. The singer reported only slight intrusion of the physical presence of the tablet on enunciation.

Example P

On his own volition, the singer of Example O applied a small amount of the oral gel from Example 2 around the rim of a water glass placed as usual within easy reach behind him onstage. The singer observed that unobtrusively touching his tongue to the gel just after a sip of water and distributing the gel around his mouth with his tongue as he turned back to the audience, kept his oral cavity moisturized for about six songs. By repeating this application once or twice more, his full program could be sung with a moisturized mouth. This utility method had absolutely no intrusion on the enunciation or intonation of his singing.

Example Q

A 60-year-old female incurred breast cancer procedure requiring 15 rounds of chemo and radiation dermatitis after breast surgery. One week after last radiation treatment, the skin was red, scaly and itched. The painful itching prevented normal sleep patterns. Skin lotions and steroid creams did not help. Skin cream from Example 3 was applied in pea-sized amounts daily over 4 weeks to the surgical site beginning one week after last radiation treatment. Subject was able to sleep through the night on day one without itching. Redness was greatly diminished after three days. After four weeks, the skin had returned to normal color without any itching or redness.

Example R

A 58 year old female reported that she was experiencing occasional psoriatic skin on the bridge of the nose. She was supplied with lotion of Example 1. She also was experiencing dry eyes which often accompanies dry mouth and took it upon herself to carefully apply small amounts of this lotion to areas around the eye and small amounts on the eye lid. She observed reduced dry eye symptoms. She continues to use the lozenges and skin cream daily.

Example S

A 50 year old male experienced stress-induced episodes of migraine headaches five to six times/year, each preceded by a "trigger signal" of slight dizziness or light-headedness. Sumatriptan prescription was slow to relieve the pain. The lotion of Example 1 was applied by the subject in pea-sized amounts to the forehead and temples. The application caused the trigger sensation to recede within 30 minutes and the migraine did not develop. No migraine episodes have occurred in the past eight months.

Example T

A panel of 5 trained organoleptic evaluators evaluated the following properties of the Oral Conditioner Rinse of EXAMPLE 9. Results are Panel Averages: Scale of 1-5.

| Organoleptic Properties | Initial Intensity (1-5) | Time Perceived (min) |
|---|---|---|
| PLEASANTNESS | 4.3 | 12 |
| CLEAN TEETH/MOUTH | 4.1 | 65 |
| SMOOTH MUCOSA | 4.5 | 57 |
| COMFORTABLE | 5.0 | 64 |
| MOISTURE | 4.8 | 37 |

Example U

A 55 year old female nurse had suffered for many years with Crohn's disease, in which psoriasis on the knees and elbows occurred before each flare-up of abdominal pain. For many years her Crohn's incidence of abdominal pain, was sufficient to prevent normal attendance at work. She was being treated by a gastroenterologist who found and removed the typical intestinal growths on multiple occasions. The frequency of flair-ups was about one to two times per month on a regular basis. Subject subsequently developed dry mouth and dry throat, to the extent that her voice began to fail, greatly interfering with her occupation as a teaching nurse. She was given lozenges of Example 8 to relieve dry mouth symptoms. The instant relief from Dry Mouth symptoms occurred with each lozenge. Over a three-month period of using 4-5 lozenges per day, she remarked that the Crohn's symptoms seemed to diminish. And over the next 3 months her voice repaired sufficiently to return to daily lecturing. She reported that she had not had a Crohn's flair-up for the last three months. Upon inquiry about the frequency of psoriasis, she reported that they occasionally returned but were not followed by the dreaded flair-up. The psoriasis sites were still the typical i.e., red, scaly, itching psoriasis sores on elbows and knees. She was provided with the lotion of Example 1 and began applying it to the sites twice daily as soon as she felt them starting to develop. The psoriasis development continued to occur, even though the pain of a Crohn's flare-up did not develop, but the lotion reduced the eruption to pink, non-scaly, non-itching, minor blemishes of short duration. At last report, she had experienced no Crohn's flare-up over the last 18 months.

Example V

A male Lawn Maintenance Contractor in his late 50's got into a patch of Poison Ivy early in the morning while operating his Weed Whacker which threw bits of stem and leaves on his forearms and one spot on his forehead. By noon, at his next job site, he presented a serious itching problem and there were several individual "bumps" like he has experienced before all over his forearms and two on his forehead. There was also a "streak" on the underside of his forearm already broken out and red which likely came from the sap end of a stem cutting. He was given an Example 1 skin cream to rub generously over the itching areas, including those exposed and itching but had not yet produced a visible lesion. Within minutes of washing his hands, the subject was saying amazedly "No More Itching! No More Itching". There were no additional visible lesions after 3 hours when he finished the job. At noon the following day, the subject reported that the Poison Ivy lesions had not developed further and there was still no itching.

Example W

A 47-year-old male tested positive (nasal swab test) for COVID-19 after a temperature of 103 degrees, loss of taste and smell, persistent cough, diarrhea and intense fatigue. The cough prevented restful sleep for 3 days. Lozenges of Example 8 were then used 5 times a day and allowed to dissolve slowly in the mouth along with application of a topical cream of Example 3, applied to his neck area 4 times per day. The cough stopped after 8 hours. The cough did not return and after a two-week period of isolation, he tested negative and returned to work.

Example X

Gingival Healing with OTC Rinse and Oral Gel

A 31-year-old male with serious painful gingival inflammation requiring periodontal surgery was prescribed 10 days of twice-daily rinsing with a stable glycerin solution in Stannous Fluoride diluted to FDA standard concentrations for OTC use with a diluent consisting of the ingredients in Example 2. Major gingival surgery was performed, and the subject received an Oral Gel of Example 2 with instructions to rub the gel on all gingival surfaces, even those not subjected to surgery, on arising. Inspection after 3 days showed healing of a quality normally only observed after 10 days.

Example Y

Shingles Itch and Pain Relief

A 77-year-old male observed small red blisters on his right knee after 3 days of backache. A photo of these blisters was provided to his doctor. A prescription was obtained and taken for valacyclovir, 1 gm, three times daily for 7 days. The red blisters were in a cluster of one inch on the right knee. A pea-sized amount of the cream was massaged into the area of the blisters on day one. The next day, the original blisters were less red, but three additional one-inch groupings were observed and treated as before. The subsequent days many smaller shingles blisters randomly appeared over the top and side of the right thigh. Treatment of these larger areas with the skin cream twice daily showed reduced redness and size each day, until by day 10, no new blisters appeared. The skin cream applications stopped, and the redness continued to diminish over the next two weeks. No itching or pain was experienced during this time.

Example Z

Osteoarthritis Pain Relief

A 74-year-old male experienced severe pain in his right knee after stepping on a rock. The pain persisted over two weeks and made it difficult to walk and rise from a seated position. An orthopedic specialist diagnosed the knee problem after x-rays as osteoarthritis. The patient mentioned using a custom-made pain cream that gave him relief. The specialist said if it gives you relief, to keep on using it. The cream of Example 4 was used as needed for pain and gave relief within minutes of the knee pain and allowed rising from a seated position without pain. After three weeks of usage, the pain did not reoccur, and the cream was discontinued. Over the next year, when the knee was stressed, the pain cream of Example 4 gave immediate relief.

From the foregoing, it will be appreciated that although specific examples have been described herein for purposes of illustration, various modifications, obvious to one skilled in the art, may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

All references and other documents cited above are hereby incorporated herein by reference in their entirety.

What is claimed is:

1. A method of treating a subject in need of pain relief, the method comprising:
    administering to the skin of a subject an effective amount of a composition to relieve a painful condition, the composition comprising: a mixture of spilanthol in the range of 0.1 wt % to 0.5% wt %, pellitorine in the range of 0.05 wt % to 0.2 wt %, beta-caryophyllene in the range of 1 wt % to 3 wt %, and pro-vitamin B5 in the range of 2 wt % to 6 wt %,
    wherein the composition is in a topical formulation including cream, gel, or lotion,
    wherein the non-vitamin components of the mixture are in an amount of from 0.01 mg to 1000 mg, and
    wherein the vitamin component of the mixture is in an amount of from 1.5 mg to 1000 mg.

2. The method of claim 1, wherein the composition further comprises 0.02 wt % to 3 wt % menthol.

3. The method of claim 1, wherein the painful condition is caused by or related to a body condition selected from the group consisting of: Sjogren's Syndrome, Chronic and Acute Pain of the muscles, joints and ligaments, Migraine Headaches, Diabetes, Arteriosclerosis, Radiation Dermatitis, Pruritus, Insect bites, Anaphylactic Shock from serious allergic responses to allergens from Insect Bites, Food Allergies, Pollens and other Environmentally induced allergies, Carbuncles, Acne, Dermal burns due to exposure to sun, x-rays and/or excessive heat, Cancer, Mucositis, Aphthous ulcers, Periodontal and Gingivitis disease, Herpes simplex, Herpes zoster, Coronavirus-19, Yeast and/or Microbial infections, Psoriasis, Crohn's disease, Lupus, painful scarring, Irritable Bowel disease, other Autoimmune Diseases and Diseases causally related to autoimmune diseases like fibromyalgia, Rheumatoid and Osteoarthritis, and Xerostomia.

4. The method of claim 1, wherein the painful conditions are controlled by affecting one or more biochemical control systems selected from the group consisting of Annexin A1, NRF2, NFKB, PI3K, AKT, p38-MAPK, JNK, PIP2, PIP3, ERK1h, CAMP, Adenylyl cyclase, TRPV1, TRPA1, TRPM8, PGE2, IL-1b, CXCR4, CXCL12 and CB2.

5. The method of claim 1, wherein the vitamin component is in an amount of from 2.5 mg to 500 mg.

6. The method of claim 1, wherein spilanthol and pellitorine are administered in an amount from 0.1 mg to 1000 mg per dose and beta-caryophyllene is administered in an amount of from 2 mg to 1000 mg.

7. The method of claim 1, wherein the painful condition is caused by or related to Alzheimer's disease.

8. A method of treating a subject in need of pain relief, the method comprising:
    administering to a subject an effective amount of a composition to relieve a painful condition, the composition comprising: a mixture of spilanthol in the range of 0.0025 wt % to 0.4 wt %, pellitorine in the range of 0.0015 wt % to 0.2 wt %, menthol in the range of 0.0005 wt % to 0.005 wt %, and pro-vitamin B5 in the range of 0.1 wt % to 0.5 wt %,
    wherein the composition is an oral formulation including a lozenge, spray, rinse, toothpaste, or tablet,
    wherein the non-vitamin components of the mixture are in an amount of from 0.01 mg to 1000 mg, and
    wherein the vitamin component of the mixture is in an amount of from 1.5 mg to 1000 mg.

9. The method of claim 8, wherein the composition further comprises beta-caryophyllene.

10. The method of claim 9, wherein spilanthol and pellitorine are administered in an amount from 0.1 mg to 1000 mg per dose and beta-caryophyllene is administered in an amount of from 2 mg to 1000 mg.

11. The method of claim 8, wherein the painful condition is caused by or related to a body condition selected from the group consisting of: Alzheimer's disease, Chronic and Acute Pain of the muscles, joints and ligaments, Migraine Headaches, Diabetes, Arteriosclerosis, Radiation Dermatitis, Pruritus, Insect bites, Anaphylactic Shock from serious allergic responses to allergens from Insect Bites, Food Allergies, Pollens and other Environmentally induced allergies, Carbuncles, Acne, Dermal burns due to exposure to sun, x-rays and/or excessive heat, Cancer, Mucositis, Aphthous ulcers, Periodontal and Gingivitis disease, Herpes simplex, Herpes zoster, Coronavirus-19, Yeast and/or Microbial infections, Psoriasis, Crohn's disease, Lupus, painful scarring, Irritable Bowel disease, other Autoimmune Diseases and Diseases causally related to autoimmune diseases like fibromyalgia, Rheumatoid and Osteoarthritis, and Xerostomia.

12. The method of claim 8, wherein the painful condition is caused by or related to Sjogren's Syndrome.

13. The method of claim 8, wherein the painful conditions are controlled by affecting one or more biochemical control systems selected from the group consisting of Annexin A1, NRF2, NFKB, PI3K, AKT, p38-MAPK, JNK, PIP2, PIP3, ERK1h, CAMP, Adenylyl cyclase, TRPV1, TRPA1, TRPM8, PGE2, IL-1b, CXCR4, CXCL12 and CB2.

14. The method of claim 8, wherein the vitamin component is in an amount of from 2.5 mg to 500 mg.

15. A method of treating a subject in need of joint pain relief, the method comprising:
administering to a subject an effective amount of a composition to relieve a painful condition, the composition comprising: a mixture of spilanthol in the range of 0.05 wt % to 0.3 wt %, pellitorine in the range of 0.05 wt % to 0.3 wt %, beta-caryophyllene in the range of 1 wt % to 3 wt %, and pro-vitamin B5 in the range of 1.0 wt % to 6.0 wt %,
wherein the composition is a topical formulation including cream, gel, or lotion,
wherein the non-vitamin components of the mixture are in an amount of from 0.01 mg to 1000 mg, and
wherein the vitamin component of the mixture is in an amount of from 1.5 mg to 1000 mg per dose.

16. The method of claim 15, wherein the composition further comprises 0.1 to 3 wt % menthol.

17. The method of claim 15, wherein spilanthol and pellitorine are administered in an amount from 0.1 mg to 1000 mg per dose and beta-caryophyllene is administered in an amount of from 2 mg to 1000 mg.

18. The method of claim 15, wherein the painful condition is caused by or related to a body condition selected from the group consisting of: Alzheimer's disease, Sjogren's Syndrome, Chronic and Acute Pain of the muscles, joints and ligaments, Migraine Headaches, Diabetes, Arteriosclerosis, Radiation Dermatitis, Pruritus, Insect bites, Anaphylactic Shock from serious allergic responses to allergens from Insect Bites, Food Allergies, Pollens and other Environmentally induced allergies, Carbuncles, Acne, Dermal burns due to exposure to sun, x-rays and/or excessive heat, Cancer, Mucositis, Aphthous ulcers, Periodontal and Gingivitis disease, Herpes simplex, Herpes zoster, Coronavirus-19, Yeast and/or Microbial infections, Psoriasis, Crohn's disease, Lupus, painful scarring, Irritable Bowel disease, other Autoimmune Diseases and Diseases causally related to autoimmune diseases like fibromyalgia, Rheumatoid and Osteoarthritis, and Xerostomia.

19. The method of claim 15, wherein the painful conditions are controlled by affecting one or more biochemical control systems selected from the group consisting of Annexin A1, NRF2, NFKB, PI3K, AKT, p38-MAPK, JNK, PIP2, PIP3, ERK1h, CAMP, Adenylyl cyclase, TRPV1, TRPA1, TRPM8, PGE2, IL-1b, CXCR4, CXCL12 and CB2.

20. The method of claim 15, wherein the vitamin component is in an amount of from 2.5 mg to 500 mg.

* * * * *

UNITED STATES PATENT AND TRADEMARK OFFICE
CERTIFICATE OF CORRECTION

| | | |
|---|---|---|
| PATENT NO. | : 12,303,476 B2 | Page 1 of 1 |
| APPLICATION NO. | : 18/383606 | |
| DATED | : May 20, 2025 | |
| INVENTOR(S) | : Dale G. Brown and Ira D. Hill | |

It is certified that error appears in the above-identified patent and that said Letters Patent is hereby corrected as shown below:

In the Specification

In Column 5, Line 67, replace "0.5% wt %" with --0.5 wt %-- and

In the Claims

In Claim 1, Column 13, Line 62, replace "0.5% wt %" with --0.5 wt %--

Signed and Sealed this
Twenty-sixth Day of August, 2025

Coke Morgan Stewart
*Acting Director of the United States Patent and Trademark Office*